(12) United States Patent
Welch (10) Patent No.: US 9,902,667 B2
(45) Date of Patent: Feb. 27, 2018

(54) METHOD FOR REDUCING ENERGY CONSUMPTION IN A PROCESS TO PURIFY STYRENE MONOMER

(71) Applicant: Technip Process Technology, Inc., Houston, TX (US)

(72) Inventor: Vincent Welch, Cambridge, MA (US)

(73) Assignee: Technip Process Technology, Inc., Houston, TX (US)

( * ) Notice: Subject to any disclaimer, the term of this patent is extended or adjusted under 35 U.S.C. 154(b) by 72 days.

(21) Appl. No.: 14/652,563

(22) PCT Filed: Dec. 19, 2012

(86) PCT No.: PCT/US2012/070494
§ 371 (c)(1),
(2) Date: Jun. 16, 2015

(87) PCT Pub. No.: WO2014/098816
PCT Pub. Date: Jun. 26, 2014

(65) Prior Publication Data
US 2015/0336859 A1     Nov. 26, 2015

(51) Int. Cl.
| C07C 7/04 | (2006.01) |
| C07C 5/333 | (2006.01) |
| C07C 5/327 | (2006.01) |

(52) U.S. Cl.
CPC .............. *C07C 5/333* (2013.01); *C07C 5/327* (2013.01); *C07C 7/04* (2013.01)

(58) Field of Classification Search
CPC ............ C07C 5/333; C07C 7/04; B01D 3/146
USPC ................ 585/440, 435, 655, 805, 800, 804
See application file for complete search history.

(56) References Cited

U.S. PATENT DOCUMENTS

| 3,558,729 | A | | 1/1971 | De Graff | |
| 4,469,558 | A | * | 9/1984 | Watson | B01D 3/146 |
| | | | | | 202/154 |
| 4,615,769 | A | * | 10/1986 | Horigome | C07C 7/04 |
| | | | | | 202/182 |
| 5,386,075 | A | | 1/1995 | Keil et al. | |
| 5,866,740 | A | * | 2/1999 | Mikitenko | C07C 7/005 |
| | | | | | 585/470 |
| 6,096,941 | A | | 8/2000 | Art | |

(Continued)

OTHER PUBLICATIONS

PCT Notification Concerning Transmittal of International Preliminary Report on Patentability (Chapter I of the Patent Cooperation Treaty) dated Jul. 2, 2015; PCT International Preliminary Report on Patentability (Form PCT/IB/373); and PCT Written Opinion of the International Searching Authority (Form PCT/ISA/237).

(Continued)

*Primary Examiner* — Philip Louie
*Assistant Examiner* — Aaron Pierpont
(74) *Attorney, Agent, or Firm* — Locke Lord LLP; Alan B. Clement; Peter J. Fallon (57) ABSTRACT

An energy conservation process directed to the purification of styrene monomer via distillation after the dehydrogenation reaction of ethylbenzene to produce crude styrene is disclosed. As practiced today, the purification of styrene via distillation requires large amounts of energy (i.e., steam) to provide heat to the various distillation columns. The presently disclosed improved process allows for a reduction in the amount of steam needed for this purpose.

18 Claims, 3 Drawing Sheets

(56) References Cited

U.S. PATENT DOCUMENTS

| | | | | |
|---|---|---|---|---|
| 6,171,449 B1 * | 1/2001 | Welch | ............... | B01D 3/146 |
| | | | | 202/154 |
| 6,348,136 B1 * | 2/2002 | Ledoux | ............ | B01D 3/141 |
| | | | | 202/154 |
| 2009/0062588 A1 * | 3/2009 | Kowaleski | ......... | B01J 23/002 |
| | | | | 585/663 |
| 2010/0111785 A1 | 5/2010 | Oleksy et al. | | |

OTHER PUBLICATIONS

M.E. Gheshlaghi et el., "Study and Simulation Towers Performance of the Styrene Monomer Unit," American Journal of Advanced Scientific Research, (Oct. 31, 2012), vol. 1, No. 4, pp. 137-145.
PCT International Search Report (2 pages; Form PCT/ISA/210).

* cited by examiner

METHOD FOR REDUCING ENERGY CONSUMPTION IN A PROCESS TO PURIFY STYRENE MONOMER

TECHNICAL FIELD

This invention relates to energy-consumption improvements in processes to purify styrene monomer.

BACKGROUND

The majority of styrene monomer produced commercially is prepared by the dehydrogenation of ethylbenzene in a vapor phase, fixed catalyst-bed reactor. Each pass through the reactor converts about 60 to 75% of the ethylbenzene feed to styrene. The dehydrogenation reaction of ethylbenzene yields a crude styrene stream which is a mixture containing substantial portions of styrene and ethylbenzene as well as smaller amounts of reaction by-products and impurities, such as, benzene, toluene, alpha-methyl styrene (AMS) and heavies. To produce saleable styrene monomer product, the non-styrene components must be separated from the styrene product via distillation. Styrene monomer must be purified to a concentration of at least 99% by weight before it can be used by downstream polymer processes. The main components to be separated from styrene in the purification process are benzene, toluene, un-reacted ethylbenzene, AMS and heavies that are referred to as residue (i.e., compounds that are in the $C_{10}$ to $C_{141}$ range).

The current practice in the industry is to use a minimum of three distillation columns to obtain the aforementioned level of styrene product purity. The function of the distillation columns is to recover the benzene/toluene byproduct, the unreacted ethylbenzene, and separate AMS and heavier residue compounds from the styrene product. Overall the distillation process requires a large amount of energy (steam) to purify the styrene product.

Moreover, the separation by distillation of the styrene monomer (SM) from the unreacted ethylbenzene (EB) presents a considerably difficult problem due primarily to their close similarity in volatility. In this regard, the boiling points of ethylbenzene and styrene are within approximately 10° C. of each other at 760 mm Hg, which makes separation by fractional distillation difficult and costly. Conventionally, this EB/SM separation has been accomplished by distillation under vacuum conditions in large, sophisticated, and expensive distillation columns due to the large number of theoretical plates required to effect a good separation. In the conventional distillation process, unreacted ethylbenzene from the dehydrogenation reaction section is separated from styrene in a single distillation column. In the typical design, a large number of theoretical stages (between 85 and 115) are required to effect the required separation in an economically effective manner. This single unit operation accounts for between 70 and 80 percent of the total distillation section heat input. In a typical styrene manufacture process plant, the separation of unreacted ethylbenzene from styrene product accounts for approximately 20-30% of the entire plant's steam consumption.

Additional problems associated with the distillation of the styrene monomer are related to the styrene monomer's inherent reactivity. Because the styrene monomer polymerizes even at ambient temperatures forming insoluble solids, this undesirable reactivity makes distillation of the styrene monomer challenging. Since the rate of styrene polymerization increases with increase in temperature, conventional practice involves operating the distillation columns of commercial styrene plants at low pressures to reduce boiling temperatures and thereby reduce the extent of adverse polymerization.

As a result of these various process difficulties, and in particular, the associated large energy consumption requirements and costs, considerable incentive has existed for many years to develop alternative means of effecting this separation process, which is more viable from economic and ease of operation standpoints. A number of patents have attempted to address these problems in a variety of ways.

U.S. Pat. No. 6,171,449 teaches methods of energy consumption improvements by recovering at least a portion of the heat contained in an EB/SM splitter overhead stream via use of a cascade reboiler scheme in which the separation of ethylbenzene and styrene is carried out in two parallel distillation columns operating at different pressures, with the overhead of the high pressure column providing the heat required to reboil the low pressure column. U.S. Pat. No. 4,628,136 teaches a method of recovering the heat contained in the overhead of the EB/SM splitter by using this stream to boil an azeotropic mixture of ethylbenzene and water, which, once vaporized, is subsequently transferred to the reaction system where dehydrogenation of ethylbenzene to styrene takes place. The method described in the U.S. Pat. No. 4,628,136, however, requires that the EB/SM splitter operate at a pressure that is sufficiently high as to enable the transfer of the azeotropic mixture of ethylbenzene and water vapor into the reactor system without the use of a compressor. This patent also specifies that the temperature difference between the condensing EB/SM splitter overhead and the boiling azeotropic mixture of ethylbenzene and water should be in the range of between and 2 and 10° C. Given this temperature constraint, one can derive a relationship between the pressure at which the azeotropic vaporization is taking place and the required overhead pressure of the EB/SM splitter.

For economic reasons it is desirable to lower the amount of steam (i.e., energy) requirements in the process to purify styrene monomer. Thus, in view of the above, it would be beneficial to have a method of reducing the steam usage while also having the ability to independently add heat into the process.

EMBODIMENTS OF THE INVENTION

Accordingly, an embodiment of the invention is directed to an improved process for the purification of styrene monomer via distillation after the dehydrogenation reaction of ethylbenzene to produce crude styrene.

According to another embodiment, the invention is directed to a process for significantly reducing the utility costs associated with the normally energy intensive unit operation of distillation separation of ethylbenzene and styrene.

Yet according to another embodiment, the invention is directed to an efficient and economical approach to separating styrene product from other components of the crude styrene stream coming from an ethylbenzene dehydrogenation reaction by reducing the amount of steam required to heat one distillation column by using the overhead vapor of another distillation column instead of steam.

According to still another embodiment the invention is directed to a relatively easy and low cost adaptation for existing styrene plants to increase operating efficiency and reduce energy consumption.

Other objects and advantages of the present invention will in part be obvious and will in part appear hereinafter. The invention accordingly comprises, but is not limited to, the processes and related apparatus, involving the several steps and the various components, and the relation and order of one or more such steps and components with respect to each of the others, as exemplified by the following description and the accompanying drawing. Various modifications of and variations on the process and apparatus as herein described will be apparent to those skilled in the art, and all such modifications and variations are considered within the scope of the invention.

SUMMARY OF THE INVENTION

In general, this invention comprises a cascaded arrangement of two distillation processes whereby heat contained in the overhead vapor stream of one distillation process is utilized to reboil the entire bottoms liquid or a portion of the bottoms liquid of a second distillation process. More specifically, this invention is directed to a process for distilling benzene and toluene from ethylbenzene in one distillation process, and styrene monomer from AMS and residue in another distillation process, and utilizing the heat contained in the overhead vapor stream of one distillation process to entirely reboil or partially reboil the bottoms liquid of the second distillation process. The resultant synergisms in process integration and thermal efficiency result in substantially lower energy costs as well as other related savings.

The present invention is directed to a process for reducing the energy required to purify styrene monomer from a feedstock containing ethylbenzene. The process comprising i) dehydrogenating said feedstock to provide a crude styrene stream containing styrene, ethylbenzene, benzene, toluene, alpha-methyl styrene, and heavies; ii) purifying the crude styrene stream in a series of distillation processes, wherein a first distillation process provides a first distillation overhead stream comprising benzene and toluene and a first distillation bottoms stream comprising ethylbenzene, and second distillation process utilizing at least one reboiler provides a second distillation overhead comprising purified styrene monomer and a second distillation bottoms stream comprising alpha-methyl styrene and heavies; iii) withdrawing at least one reboiler stream from the second distillation bottoms stream and reboiling the reboiler stream in the reboiler; and iv) providing heat to the reboiler by indirect contact with the first distillation overhead stream, wherein said reboiler stream enters the reboiler at a temperature that is equal to or less than the temperature of the first distillation overhead stream exiting said reboiler.

A process for reducing the energy required to purify styrene monomer from a feedstock containing ethylbenzene. The process comprises: i) dehydrogenating the feedstock to provide a crude styrene stream containing styrene, ethylbenzene, benzene, toluene, alpha-methyl styrene, and heavies; ii) purifying the crude styrene stream in a series of distillation processes, wherein a first distillation process provides a first distillation overhead stream comprising benzene and toluene and a first distillation bottoms stream comprising ethylbenzene, and second distillation process utilizing at least a first reboiler and a second reboiler provides a second distillation overhead comprising purified styrene monomer and a second distillation bottoms stream comprising alpha-methyl styrene and heavies; iii) withdrawing at least a first reboiler stream and a second reboiler stream from the second distillation bottoms stream and reboiling the first reboiler stream in the first reboiler and the second reboiler stream in the second reboiler; and iv) providing heat to the first reboiler by indirect contact with the first distillation overhead stream and heat to the second reboiler by indirect contact with a heat source other than the first distillation overhead stream, wherein the first reboiler stream enters the first reboiler at a temperature that is equal to or less than the temperature of the first distillation overhead stream exiting said reboiler.

The improvements disclosed herein are substantial in terms of their economic impact, i.e., from 20 to 100 percent reduction in the amount of reboiled duty performed by the standard styrene finishing column bottoms heat exchanger, i.e., reboiler. Just as importantly, these improvements do not require fundamental changes to the process. Therefore, it is anticipated that there will be little resistance to adopting them.

BRIEF DESCRIPTION OF THE DRAWING

FIG. 1 is a schematic process flow chart illustrating a conventional distillation apparatus for the purification of styrene monomer.

DETAILED DESCRIPTION OF EMBODIMENTS OF THE INVENTION

FIG. 1 presents a schematic flow chart illustrating a typical distillation apparatus and purification process for crude styrene. In FIG. 1, typically from an upstream ethylbenzene dehydrogenation unit (not shown), crude styrene is fed to an ethylbenzene/styrene (EB/SM) splitter column T1. In this scenario, the benzene, toluene, and ethylbenzene are separated from styrene, AMS, and residue. The benzene, toluene, and ethylbenzene are removed from the top of the EB/SM splitter column T1, as overheads product, and styrene, AMS, and residue, i.e., compounds that are in the $C_{10}$ to $C_{14}$-range, are removed from the bottoms liquid of the EB/SM splitter column T1 as bottoms product. The bottoms product is directed to a styrene finishing column T3.

The contents of the EB/SM splitter column T1 is reboiled by taking a reboiler stream from the bottoms liquid of the EB/SM splitter column T1 and reboiling the reboiler stream using steam in the ethylbenzene/styrene splitter reboiler R1. The overhead vapor of the EB/SM splitter column T1 is condensed against cooling water in the ethylbenzene/styrene (EB/SM) splitter condenser C1. Part of the condensed overhead from EB/SM splitter condenser C1 is sent back to the EB/SM splitter column T1 as reflux and the remainder is the benzene/toluene/ethylbenzene distillate, which is sent to a benzene/toluene column T2. In the benzene/toluene column T2, the benzene and toluene are separated from the ethylbenzene and heavier components, which is withdrawn from the bottoms liquid of column T2 and recycled back to the dehydrogenation unit (not shown). The bottoms liquid of the benzene/toluene column T2 is reboiled by taking a reboiler stream from the bottoms liquid and reboiling the reboiler stream using steam in a benzene/toluene column reboiler R2. The benzene/toluene column T2 overhead vapor, i.e., overheads containing benzene and toluene, is condensed against cooling water in the benzene/toluene column condenser C2. Part of the condensed overhead from the benzene/toluene column condenser C2 is sent back to the benzene/toluene column T2 as reflux and the remainder is recovered as benzene/toluene by-product.

The function of the styrene finishing column T3 is to restrict the amount of AMS and residue in the final styrene product which is recovered at the top of the styrene finishing column T3. The bottoms liquid of the styrene finishing column T3 is reboiled by taking a reboiler stream from the bottoms liquid and reboiling the reboiler stream using steam in the styrene finishing column reboiler R3 (i.e., thermal exchange means), and the styrene finishing column T3 overhead vapor is condensed against cooling water in the styrene finishing column condenser C3. Part of the condensed overhead from the styrene finishing column condenser C3 is sent back to the column T3 as reflux and the remainder is recovered as the final styrene product.

The conventional distillation apparatus and purification process typically has a residue flash pot V1 or other devices that vaporizes the styrene finishing column T3 bottoms liquid in order to minimize the amount of styrene lost to the residue stream. In this example, heat input to the residue flash pot V1 is provided by steam in the residue reboiler R4.

Table 1 provides typical operating pressure ranges for each of the aforementioned columns.

TABLE 1

| Typical Overhead Operating Pressures for Columns presentedin FIG. 1 | | | |
| --- | --- | --- | --- |
|  | T1 | T2 | T3 |
| mmHg (a) | 10-1000 | 10-2500 | 10-1000 |

Figure 2:
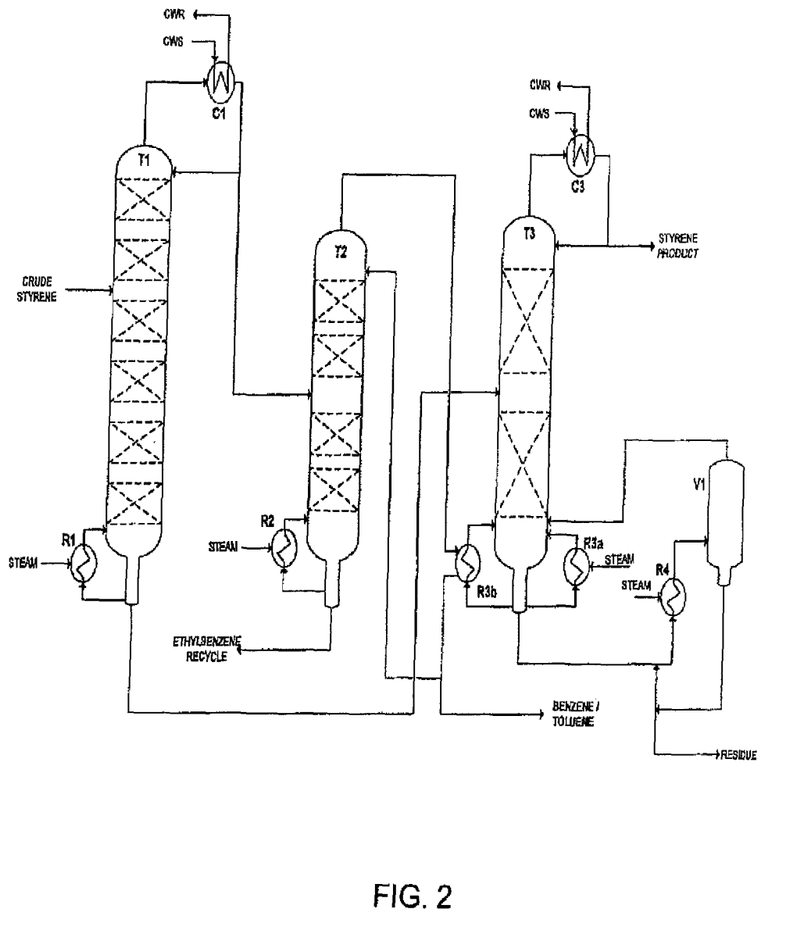
FIG. 2 is a schematic process flow chart illustrating a distillation apparatus for the purification of styrene monomer according to an embodiment of the present invention.

Turning to FIG. 2, which presents a schematic process flow chart illustrating a distillation apparatus for the purification of styrene monomer according to an embodiment of the invention. FIG. 2 presents the styrene finishing column T3 of the claimed improved process having two reboilers R3a and R3b. The two reboilers R3a and R3b reboil the bottoms liquid utilizing two separate reboiler streams. The two separate reboiler streams are taken from a bottoms stream provided by the styrene finishing column T3 bottoms liquid. In this scenario, heat is provided to reboilers (R3a and R3b) by two sources. The first heat source is steam, which is supplied to primary styrene finishing column T3 reboiler R3a, and the second source of heat is the heat from the benzene/toluene column T2 overhead vapor overheads that is supplied to styrene finishing column T3 reboiler R3b. In this embodiment, it is understood that either reboiler R3a or R3b can be the primary styrene finishing column T3 reboiler, as long as one of the styrene finishing column T3 reboilers is supplied with heat utilizing the heat from the overheads of the benzentholuene column T2. Thus, the amount of steam required to provide heat to the styrene finishing column T3 is significantly reduced.

FIG. 2 merely represents one example of many possible distillation apparatus for the purification of styrene monomer according to an embodiment of the invention. Other examples include, but are not limited to: alternative sources of heat input to styrene finishing column T3 reboiler R3a, for example, from the overheads of EB/SM splitter column T1; heat from the overheads of benzene/toluene column T2 provides the entire heat required to reboil the bottoms liquid of styrene finishing column T3; and heat from the overheads of EB/SM splitter column T1 T1 could be used in place of the overheads of benzene/toluene column T2 as described herein above.

FIG. 2 presents one example of the internals that can be used in the distillation columns T2 and T3, i.e., packing. Distillation separation technology involves a flow of a liquid phase and a vapor phase in opposite directions, which are brought into intimate contact to realize a mass transfer between both phases. Mass transfer between liquid and vapor takes place at the interface of the phases. In order to establish and maximize the interface, separating internals are mounted in the distillation columns, for example, mass transfer trays, random packing material, structured packing, or some combination of the previous listed separating internals.

All types of packing, such as, structured packing, random/dump packing, and gauze packing, can be used in the claimed invention. Structured packing is defined herein as geometric arrangements of formed sheet metal layers or fabric layers which are fixedly secured in the distillation column. Compared to conventional mass transfer (distillation) trays, packing exhibits a large and specific mass transfer surface and a low pressure loss at the same time. The geometry of the packing allows that the specific mass transfer surface and the pressure loss of the packing can be tailored in a desired fashion and suited to the desired separation task. For purposes of the present disclosure the term "packing" is understood to mean any type of packing.

Combinations of internals can be used in the improved process described herein. Combination of internals includes, for example, packing in the top of the benzene/toluene and/or styrene finishing columns and trays in the bottom. As such, various combinations of internals for use with the improved process are contemplated herein. As known in the art, packing has the advantage over trays in the styrene finishing column T3 of FIG. 2 because of the minimum pressure drop across the column provided by the packing. The use of packing ensures the pressure and temperature at the bottom of the column is as low as possible. The rate of styrene polymerization is a function of temperature, thus, lower temperatures will result in less polymer formation and a lower rate of polymerization inhibitor consumption.

It should be noted that use of trays in the styrene finishing column T3, may be preferable, as trays have the benefit of being more accessible for maintenance. However, in benzene/toluene column T2, either trays or packing can provide reliable operation as there is less concern about the bottoms pressure and temperature because only small concentrations of styrene are present.

The claimed process can utilize various types of heat exchangers to reboil the bottoms liquid of the styrene finishing column T3. Typically, in styrene distillation and purification methods, thermosiphon type heat exchangers are used as reboilers. Thermosiphon reboilers are economical in that they require the least amount of surface area making the heat exchanger smaller and requiring no additional support equipment, such as, for example, pumps. Other types of heat exchangers can be used, including, but not limited to, falling film heat exchangers or pump through exchangers.

In the case of the instantly claimed process, the overheads from benzene/toluene column T2 are used as the heating medium to reboil a reboiler stream from the styrene finishing column T3 bottoms liquids in the styrene finishing column reboiler R3b. The temperature differential between the overheads after leaving the styrene finishing column reboiler R3b and the reboiler stream entering reboiler R3b is relatively small. In this regard, the presently claimed process requires the temperature of the reboiler stream entering the reboiler R3b of the styrene finishing column T3 to be substantially the same as, or less than the temperature of the overheads from benzene/toluene column T2 after it has left the styrene finishing column reboiler R3b.

T2 overheads after exiting heat exchanger R3b and the reboiler stream of styrene fining column T3 entering reboiler R3b, respectively.

TABLE 2

T2 and T3 Operating Pressures and Temperatures with R3b temperature differentials approach

| Examples | | 1 | 2 | 3 | 4 | 5 | 6 | 7 |
|---|---|---|---|---|---|---|---|---|
| T2 Internals | | Packing | Packing | Packing | Packing | Packing | Trays | Trays |
| T2 Overheads Temperature | ° C. | 89 | 91 | 96 | 99 | 106 | 99 | 106 |
| T2 Overheads Pressure | mmHg(a) | 500 | 530 | 610 | 683 | 825 | 683 | 825 |
| T2 Bottoms Temperature | ° C. | 122 | 124 | 129 | 133 | 140 | 143 | 149 |
| T2 Bottoms Pressure | mmHg(a) | 515 | 545 | 625 | 698 | 840 | 908 | 1050 |
| T3 Internals | | Packing | Packing | Packing | Packing | Packing | Packing | Packing |
| T3 Overheads Temperature | ° C. | 58 | 58 | 58 | 63 | 63 | 63 | 63 |
| T3 Overheads Pressure | mmHg(a) | 35 | 35 | 35 | 45 | 45 | 45 | 45 |
| T3 Bottoms Temperature | ° C. | 74 | 74 | 74 | 78 | 78 | 78 | 78 |
| T3 Bottoms Pressure | mmHg(a) | 55 | 55 | 55 | 65 | 65 | 65 | 65 |
| **R3b Temperature Approach | ° C. | 1 | 3 | 8 | 8 | 15 | 8 | 15 |

| Examples | | 8 | 9 | 10 | 11 | 12 | 13 | 14 |
|---|---|---|---|---|---|---|---|---|
| T2 Internals | | Packing | Packing | Packing | Packing | Packing | Trays | Trays |
| T2 Overheads Temperature | ° C. | 109 | 112 | 115 | 120 | 125 | 126 | 142 |
| T2 Overheads Pressure | mmHg(a) | 890 | 970 | 1070 | 1215 | 1385 | 1425 | 2100 |
| T2 Bottoms Temperature | ° C. | 143 | 146 | 150 | 155 | 161 | 168 | 183 |
| T2 Bottoms Pressure | mmHg(a) | 905 | 985 | 1085 | 1230 | 1400 | 1650 | 2325 |
| T3 Internals | | Packing | Packing | Comb.* | Comb.* | Comb.* | Comb.* | Trays |
| T3 Overheads Temperature | ° C. | 75 | 58 | 58 | 63 | 75 | 63 | 63 |
| T3 Overheads Pressure | mmHg(a) | 75 | 35 | 35 | 45 | 75 | 45 | 45 |
| T3 Bottoms Temperature | ° C. | 88 | 74 | 98 | 100 | 105 | 100 | 117 |
| T3 Bottoms Pressure | mmHg(a) | 95 | 55 | 140 | 150 | 180 | 150 | 260 |
| **R3b Temperature Approach | ° C. | 8 | 25 | 5 | 8 | 8 | 15 | 15 |

"*Comb." internals are a combination of packing in the top of the column and trays in the bottom "**R3b Temperature Approach" (i.e., the temperature approach) is the temperature differential between the cooled benzene/toluene column T2 overheads after exiting heat exchanger R3b and the reboiler stream of styrene finishing column T3 entering the reboiler R3b, respectively This temperature difference between reboiler stream of the styrene finishing column T3 and the overheads of the benzene/toluene column after it leaves the styrene finishing column reboiler is referred to as the "temperature approach" herein, and can be adjusted for various types of reboilers (i.e., heat exchangers), as well as the distillation columns internals and various temperatures and pressures that are used in the energy saving process claimed herein.

As understood herein, the reboiled duty is the enthalpy change across the reboiler and "duty" as defined herein is the amount of heat (i.e. thermal energy) transferred per unit time (i.e. kcal/hr, BTU/hr, Megawatt).

The term "reboiler" as defined herein is a heat exchanger which is used to provide heat to the bottoms liquid of the distillation column. A reboiler is used to provide heat to at least portion of the liquid from the bottom of a distillation column (i.e., bottoms liquid) to generate vapors which are returned to the distillation column to drive the distillation separation.

Figure 3:
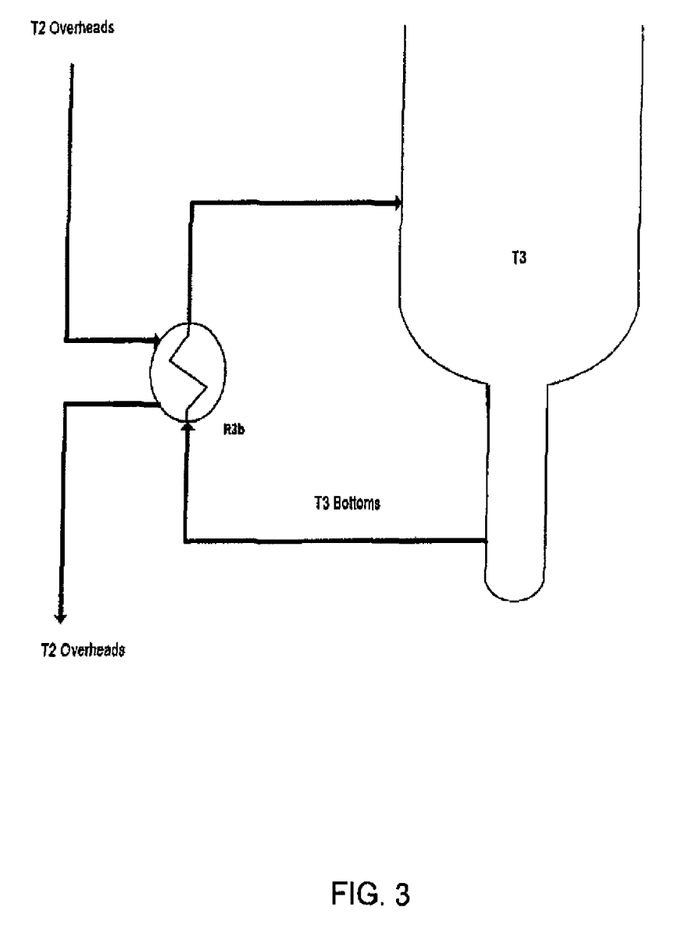
FIG. 3 is an enlarged section of the schematic process flow chart of FIG. 2 illustrating an embodiment utilizing one reboiler heat exchanger to a third distillation column.

FIG. 3 presents an enlarged section of the schematic process flow chart of FIG. 2 and illustrates an embodiment of the invention, wherein the styrene finishing column T3 utilizes only one reboiler heat exchanger R3b.

Table 2 representative Examples 1-14 presented therein, and provides a range of operating pressures and temperatures and combinations of internals used in the benzene/toluene column T2 and styrene finishing column T3 of FIG. 2. Examples 1-14 utilize different temperature approaches for styrene finishing column reboiler R3b, i.e., the temperature differential between the cooled benzene/toluene column Table 2 is arranged so as to display increasing operating temperatures and pressures in the benzene/toluene column T2 and styrene finishing column T3 of FIG. 2.

A description of the Example follows:

In Example 1, packing is used for the internals of both the benzene/toluene column T2 and styrene finishing column T3, and a temperature approach of 1° C. is used. This is an illustrative example to show that the process requires the temperature of the reboiler stream from the bottoms liquid of the styrene finishing column T3 as it enters reboiler R3b to be substantially the same as the temperature of the overheads from benzene/toluene column T2 after it has left the styrene finishing column reboiler R3b. This example is not likely to be used in practice because the capital expense would be too great, but it is theoretically possible to put this example into practice. Temperature approaches of less than 1° C. are also theoretically possible.

Example 2, the temperature approach of the styrene finishing column reboiler R3b is 3° C. which requires the temperature and pressure (operating conditions) for the benzene/toluene column T2 slightly higher than in Example 1 to maintain the higher temperature approach. This example represents more a realistic operating case.

All following examples are representative of expected operating cases.

Example 3, a temperature approach of KC is used in R3b which requires the operating conditions for benzene/toluene column T2 to be slightly than in Example 2 higher to maintain the higher temperature approach.

In Example 4, the operating conditions for the styrene finishing column are increased slightly from Example 3. As such, to maintain the same temperature approach in R3b as Example 3 the operating conditions in the benzene/toluene column are raised slightly.

Example 5, the temperature approach of the styrene finishing column reboiler R3b is 15° C. which requires the operating conditions for benzene/toluene column T2 to be slightly higher than Example 4 to maintain the higher temperature approach.

Example 6, trays are used as internals for benzene/toluene column T2 and the styrene finishing column reboiler R3b temperature approach is set at 8° C. Trays take a larger pressure drop then packing, and therefore, when comparing Example 6 to Example 3, the temperature and pressure of the benzene/toluene column T2 bottoms is required to be slightly higher in Example 6 to compensate for the additional pressure caused by the trays.

Example 7, trays are used as internals for the benzene/toluene column T2 and the styrene finishing column reboiler R3b temperature approach is set at 15° C., and in comparison to Example 6, the operating conditions in the benzene/toluene column T2 of Example 4 need to be slightly higher to maintain the greater styrene finishing column reboiler R3b approach of 15° C.

Example 8, packing is used again in both columns. Comparing Example 8 to Example 4, the operating conditions of the styrene finishing column T3 are increased by a significant amount. As such, the operating conditions of the benzene/toluene column T2 are significantly higher than in Example 4 m maintain the same temperature approach in the styrene finishing column reboiler R3b.

Example 9, the temperature approach in the styrene finishing column reboiler R3b is increased to 25° C. Comparing Example 9 to Example 3, the operating conditions of the benzene/toluene column T2 need to be significantly higher to maintain the greater styrene finishing column reboiler R3b temperature approach of 25° C.

Examples 10, 11, 12, the internals of styrene finishing column T3 are a combination of packing in the top half of the column and trays in the bottom half. As trays take more pressure drop than packing, the operating conditions of the styrene finishing column T3 bottoms are increased compared to previous examples. This also increases the operating conditions of benzene/toluene column T2. The temperature approach of the styrene finishing column reboiler is 5° C. in Example 10, and increased to 8° C. in Example 11. In Example 12 the operating conditions of the styrene finishing column are increased compared to Examples 10 and 11.

Example 13 shows operating conditions with trays in the benzene/toluene column T2, a combination of packing and trays in the styrene finishing column T3, and 15° C. temperature approach for styrene finishing column reboiler R3b.

Example 14 represents the upper limit of operating conditions for benzene/toluene column T2 and styrene finishing column T3, with trays as internals for both columns and a 15° C. temperature approach in styrene finishing column reboiler R3b.

The amount of heat that can be recovered by finishing column reboiler R3b depends on several parameters including but limited to, the number of theoretical stages (NTS) in benzene/toluene column T2, the number of theoretical stages in the styrene finishing column T3, operating pressures, concentration of toluene in the bottoms of the benzene/toluene column T2, the concentration of ethylbenzene in the overheads of the benzene/toluene column T2, the recovery of styrene in the styrene finishing column T3, and concentration of AMS in the distillate of styrene finishing column T3.

Table 3 presents Example 5 from Table 2, which is compared to Examples 15-24 having variations of the some of the above mentioned parameters.

TABLE 3

Effect of various parameters on the Heat Recovery of the Styrene Finishing Column Reboiler R3b

| Case | | 5 | 15 | 16 | 17 | 18 | 19 |
|---|---|---|---|---|---|---|---|
| T2 Internals | | Packing | Packing | Packing | Packing | Packing | Packing |
| T3 Internals | | Packing | Packing | Packing | Packing | Packing | Packing |
| T2 NTS | | 27 | 27 | 27 | 27 | 27 | 27 |
| R3b Approach | ° C. | 15 | 15 | 15 | 11 | 16 | 16 |
| Toluene Spec | wt % | 0.5 | 0.5 | 0.5 | 0.06 | 5.0 | 0.5 |
| EB Spec | wt % | 0.12 | 2.0 | 0.03 | 0.12 | 0.12 | 0.12 |
| AMS Spec | ppm | 200 | 200 | 200 | 200 | 200 | 250 |
| T2 Overhead Press | mmHg(a) | 825 | 825 | 825 | 825 | 825 | 825 |
| T2 Overhead Temp | ° C. | 106 | 107 | 106 | 106 | 106 | 106 |
| T3 Bottom Press | mmHg(a) | 65 | 65 | 65 | 65 | 65 | 65 |
| T3 Bottom Temp | ° C. | 78 | 78 | 78 | 78 | 78 | 77 |
| R3b Duty | MMkcal/hr | 3.61 | 3.43 | 4.05 | 6.77 | 1.49 | 3.61 |
| R3b Duty as % of Total T3 Reboiler Duty | % | 53 | 51 | 60 | 100 | 23 | 73 |

| Case | | 20 | 21 | 22 | 23 | 24 |
|---|---|---|---|---|---|---|
| T2 Internals | | Packing | Packing | Packing | Packing | Packing |
| T3 Internals | | Packing | Packing | Packing | Packing | Packing |
| T2 NTS | | 27 | 27 | 27 | 45 | 21 |
| R3b Approach | ° C. | 14 | 14 | 16 | 15 | 15 |
| Toluene Spec | wt % | 0.5 | 2.0 | 0.17 | 0.5 | 0.5 |
| EB Spec | wt % | 0.12 | 0.12 | 0.12 | 0.12 | 0.12 |
| AMS Spec | ppm | 150 | 50 | 250 | 200 | 200 |
| T2 Overhead Press | mmHg(a) | 825 | 825 | 825 | 825 | 825 |
| T2 Overhead Temp | ° C. | 106 | 106 | 106 | 106 | 106 |
| T3 Bottom Press | mmHg(a) | 65 | 65 | 65 | 65 | 65 |
| T3 Bottom Temp | ° C. | 79 | 80 | 78 | 78 | 78 |
| R3b Duty | MMkcal/hr | 3.61 | 2.25 | 4.98 | 3.00 | 5.71 |

TABLE 3-continued

Effect of various parameters on the Heat Recovery
of the Styrene Finishing Column Reboiler R3b

| | | | | | |
|---|---|---|---|---|---|
| R3b Duty as % of Total T3 Reboiler Duty | % | 45 | 20 | 100 | 45 | 85 |

A description of Examples 15-24 and their comparison to Example 5 is presented herein below:

In Example 15, the concentration of ethylbenzene permitted in the overheads of the benzene/toluene column T2 is increased in comparison to Example 5. The allowable ethylbenzene concentration in the overheads is increased from 0.12 weight percent (wt %) to 2.0 wt %. By increasing the concentration of ethylbenzene in the overheads of benzene/toluene column T2 the separation of benzene and toluene from ethylbenzene is made slightly easier because less of the overhead is required to be refluxed back to the benzene/toluene column T2, and the total amount of material required to be reboiled in benzene/toluene column T2 is less than in Example 5. However, less overhead flow means that the duty provided by styrene finishing column reboiler R3b is slightly lower than in Example 5.

In Example 16, the concentration of ethylbenzene permitted in the overheads of the benzene/toluene column T2 is decreased in comparison to Example 5. The allowable ethylbenzene concentration in the overheads is decreased from 0.12 wt % to 0.03 wt %. By decreasing the concentration of ethylbenzene in the overheads of benzene/toluene column T2 the separation of benzene and toluene from ethylbenzene is made slightly more difficult because more of the overhead is required to be refluxed back to the benzene/toluene column T2, and the total amount of material required to be reboiled in benzene/toluene column T2 is more than in Example 5. More overhead flow from T2 to provide duty to the styrene finishing column reboiler T3.

In Example 17, the concentration of toluene permitted in the bottoms of the benzene/toluene column T2 is decreased from 0.5 wt % in Example 5 to 0.06 wt %. By decreasing the concentration of toluene in the bottoms of the benzene/toluene column T2, the separation of benzene and toluene from ethylbenzene becomes significantly more difficult because more of the overhead is required to be refluxed back to the benzene/toluene column T2, and the total amount of material required to be reboiled in benzene/toluene column T2 is more than in Example 5. In this example, the overhead flow from T2 provides the entire duty required to reboil the styrene finishing column T3.

In Example 18, the concentration of toluene permitted in the bottoms of benzene/toluene column T2 is increased from 0.5 weight percent (wt %) in the Example 2 to 5.0 wt %. By increasing the concentration of toluene in the bottoms of benzene/toluene column T2 the separation of benzene and toluene is made slightly easier because less of the overhead is required to be refluxed back to the benzene/toluene column T2, and the total amount of material required to be reboiled in benzene/toluene column T2 is less than in Example 2. However, less overhead flow means that the duty provided by styrene finishing column reboiler R3b is lower than in Example 5.

Example 19, the toluene concentration in the bottoms of benzene/toluene column T2 is returned to 0.5 wt % and the AMS concentration allowed in the distillate of styrene finishing column T3 is increased to 250 ppm. This adjustment in the AMS concentration now provides for easier separation of styrene from AMS in the styrene finishing column T3, requires less of the overhead to be reflux back to the styrene finishing column T3, and therefore, less material is required to be reboiled.

As presented in the Example 19 results, the duty of styrene finishing column reboiler R3b has not changed from Example 5, however, the total percent of duty performed by the styrene finishing column reboiler R3b has increased significantly, i.e., from 53 percent in Example 5, to 73 percent in Example 19.

Example 20 takes an opposite approach from Example 19 and makes the separation of styrene from AMS harder in styrene finishing column T3 by decreasing the allowed concentration of AMS in the distillate of styrene finishing column T3. In Example 20, more of the overhead is refluxed back to the styrene finishing column T3, and therefore, more material is required to be reboiled. Again, the duty of styrene finishing column reboiler R3b has not changed from Example 5, but because the styrene finishing column reboiler R3b load is increased the total percentage of duty performed by styrene finishing column reboiler R3b, i.e., 45 percent, is slightly less than in Example 5.

Example 21, goes to the extremes for both the benzene/toluene column T2 and styrene finishing column T3. In Example 21, the concentration of toluene in the bottoms of benzene/toluene column T2 is increased to 2.0 wt % and the concentration of AMS in the distillate of styrene finishing column T3 is decreased to 50 ppm. When compared to Example 5, this has a two-fold effect in the negative direction. First, because the separation benzene and toluene from ethylbenzene in benzene/toluene column T2 is now much easier, there is less overhead vapor to supply duty to styrene finishing column reboiler R3b, similar to Example 18. Second, the separation of AMS from styrene in styrene finishing column T3 is now harder to achieve, and requires more total reboiler duty similar to Example 20.

Example 22 takes the opposite approach to Example 21. In Example 22, the concentration of toluene allowed in the bottoms of the benzene/toluene column T2 is decreased to 0.17 wt %, and the concentration of AMS in the distillate of the styrene finishing column T3 is increased to 250 ppm. When compared to Example 5, this has a two-fold effect in the positive direction. First, because the separation benzene and toluene from ethylbenzene in the benzene/toluene column T2 is now slightly hard, there is less overhead vapor to supply duty to styrene finishing column reboiler R3b, similar to Example 17. Second, the separation of AMS from styrene in styrene finishing column T3 is now easier to achieve, and requires less total reboiler duty similar to Example 19. In this example, the overhead flow from T2 provides the entire duty required to reboil the styrene finishing column T3.

Example 23, the number of theoretical stages (NTS) in benzene/toluene column T2 is increased by 18. This change has a similar affect as the increase in toluene concentration allowed in the bottoms of benzene/toluene column T2 in Example 18. Adding more NTS to benzene/toluene column T2 made the separation of benzene and toluene from ethylbenzene slightly easier, and therefore lowered the reflux rate and decreased the amount of overhead vapor to supply duty to styrene finishing column reboiler R3b.

Example 24, the number of theoretical stages (NTS) in benzene/toluene column T2 is increased by 6. This change has a similar affect as the decrease in toluene concentration allowed in the bottoms of benzene/toluene column T2 in Example 17. Adding more NTS to benzene/toluene column T2 made the separation of benzene and toluene from ethylbenzene slightly harder, and therefore, increased the reflux rate and decreased the amount of overhead vapor to supply duty to styrene finishing column reboiler R3b.

Although the present invention has been described in considerable detail with regard to certain versions thereof, other versions are possible, and alterations, permutations, and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A process for reducing the energy required to purify styrene, said process comprising:
   i) dehydrogenating a feedstock containing ethylbenzene to produce a crude styrene stream containing styrene, ethylbenzene, benzene, toluene, alpha-methyl styrene, and heavies;
   ii) passing the crude styrene stream to a first distillation process to separate a first distillation overhead stream comprising ethylbenzene, benzene, and toluene and a first distillation bottoms stream comprising styrene, alpha-methyl styrene, and heavies;
   iii) passing the first distillation overhead stream to a second distillation process to separate a second distillation overhead stream comprising benzene and toluene and a second distillation bottoms stream comprising ethylbenzene and substantially no styrene;
   iv) passing the first distillation bottoms stream to a third distillation process comprising at least one reboiler to separate a third distillation overhead stream comprising purified styrene and a third distillation bottoms stream comprising alpha-methyl styrene and heavies;
   v) withdrawing at least one reboiler stream from the third distillation bottoms stream and reboiling the at least one reboiler stream in the at least one reboiler; and
   vi) passing the second distillation overhead stream through the reboiler to provide heat to the at least one reboiler stream by indirect contact of the second distillation overhead stream with the at least one reboiler stream, wherein said at least one reboiler stream enters the reboiler at a temperature that is equal to or less than the temperature of the second distillation overhead stream exiting said reboiler.

2. The process according to claim 1, wherein the temperature of the second distillation overhead stream after exiting the reboiler is higher than the temperature of the reboiler stream as it enters the at least one reboiler.

3. The process according to claim 1, wherein the at least one reboiler provides 100 percent of the total heat exchanger duty for the third distillation process.

4. The process according to claim 1, wherein the first distillation process, the second distillation process, and the third distillation process each have internals.

5. The process according to claim 4, wherein the internals are packing and/or trays.

6. The process according to claim 1, wherein the pressure of the second distillation overhead stream has a range from about 10 mmHg to about 2.500 mmHg.

7. The process according to claim 1, wherein the pressure of the second distillation overhead stream has a range from about 500 mmHg to about 2100 mmHg.

8. The process according to claim 1, wherein the pressure of the third distillation overhead stream has a range from about 10 mmHg to about 1000 mmHg.

9. The process according to claim 1, wherein the pressure of the third distillation overhead stream has a range from about 25 mmHg to about 100 mmHg.

10. A process for reducing the energy required to purify styrene, said process comprising:
    i) dehydrogenating a feedstock containing ethylbenzene to produce a crude styrene stream containing styrene, ethylbenzene, benzene, toluene, alpha-methyl styrene, and heavies;
    ii) passing the crude styrene stream to a first distillation process to separate a first distillation overhead stream comprising ethylbenzene, benzene, and toluene and a first distillation bottoms stream comprising styrene, alpha-methyl styrene, and heavies;
    iii) passing the first distillation overhead stream to a second distillation process to separate a second distillation overhead stream comprising benzene and toluene and a second distillation bottoms stream comprising ethylbenzene and substantially no styrene;
    iv) passing the first distillation bottoms stream to a third distillation process comprising at least a first reboiler and a second reboiler to separate a third distillation overhead stream comprising purified styrene and a third distillation bottoms stream comprising alpha-methyl styrene and heavies;
    v) withdrawing at least a first reboiler stream and a second reboiler stream from the third distillation bottoms stream and reboiling the first reboiler stream in the first reboiler and reboiling the second reboiler stream in the second reboiler;
    vi) passing the second distillation overhead stream through the first reboiler to provide heat to the first reboiler stream by indirect contact of the first second distillation overhead stream with the first reboiler stream, wherein the first reboiler stream enters the first reboiler at a temperature that is equal to or less than the temperature of the second distillation overhead stream exiting said first reboiler; and
    vii) passing a heat source other than the second distillation overhead stream through the second reboiler to provide heat to the second reboiler stream by indirect contact of the heat source other than the second distillation overhead stream with the second reboiler stream.

11. The process according to claim 10, wherein the temperature of the second distillation overhead stream after exiting the first reboiler is higher than the temperature of the first reboiler stream as it enters the first reboiler.

12. The process according to claim 10, wherein the first and second reboiler together provide a total heat exchanger duty for the third distillation process, wherein the first reboiler provides from about 20 percent to about 100 percent of the total heat exchanger duty.

13. The process according to claim 10, wherein the first distillation process, the second distillation process, and the third distillation process each have internals.

14. The process according to claim 13, wherein the internals are packing and/or trays.

15. The process according to claim 10, wherein the pressure of the second distillation overhead stream has a range from about 10 mmHg to about 2500 mmHg.

16. The process according to claim 10, wherein the pressure of the second distillation overhead stream has a range from about 500 mmHg to about 2100 mmHg.

17. The process according to claim 10, wherein the pressure of the third distillation overhead stream has a range from about 10 mmHg to about 1000 mmHg.

18. The process according to claim 10, wherein the pressure of the third distillation overhead stream has a range from about 25 mmHg to about 100 mmHg.

\* \* \* \* \*